(12) United States Patent
Sato

(10) Patent No.: US 9,365,477 B2
(45) Date of Patent: Jun. 14, 2016

(54) METHOD FOR PRODUCING LAVANDULAL

(71) Applicant: KURARAY CO., LTD., Kurashiki-shi (JP)

(72) Inventor: Junko Sato, Tainai (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 14/778,357

(22) PCT Filed: Mar. 6, 2014

(86) PCT No.: PCT/JP2014/055802
§ 371 (c)(1),
(2) Date: Sep. 18, 2015

(87) PCT Pub. No.: WO2014/148269
PCT Pub. Date: Sep. 25, 2014

(65) Prior Publication Data
US 2016/0068457 A1    Mar. 10, 2016

(30) Foreign Application Priority Data

Mar. 19, 2013  (JP) ................. 2013-056647

(51) Int. Cl.
*C07C 45/51* (2006.01)
*C07C 45/00* (2006.01)

(52) U.S. Cl.
CPC .............. *C07C 45/00* (2013.01); *C07C 45/515* (2013.01)

(58) Field of Classification Search
CPC .................................................. C07C 45/515
USPC ....................................... 568/486
See application file for complete search history.

(56) References Cited

U.S. PATENT DOCUMENTS 3,700,717 A    10/1972   Kappeler et al.

FOREIGN PATENT DOCUMENTS

| JP | 47-30690 B1 | 8/1972 |
| JP | 2002-308815 A | 10/2002 |

OTHER PUBLICATIONS

Jun Tabata, "A convenient route for synthesis of 2-isopropyliden-5-methyl-4-hexen-1-yl butyrate, the sex pheromone of *Planococcus kraunhiae* (Hemiptera: Pseudococcidae), by use of β,γ to α,β double-bond migration in an unsaturated aldehyde," Applied Entomology and Zoology, vol. 48, No. 2, Mar. 2013, pp. 229-232.

Takashi Mino, et al., "Hydrolysis of β,γ-Unsaturated Aldehyde Dimethylhydrazones with Copper Dichloride: A new Synthesis of Lavandulol," J. Org. Chem, vol. 62, No. 3, 1997, pp. 734-735.

S. Masson, et al., "Metallation et Alkylation des Thioimidoesters: Application en Synthese," Tetrahedron, vol. 40, No. 9, 1984, pp. 1573-1580 (with English abstract).

J. Celebuski, et al., "Carbon—Carbon Bond Formation Employing Organoiron Reagents, Syntheses of Lavandulol and Red Scale Pheromone," Tetrahedron, vol. 41, No. 24, 1985, pp. 5741-5746.

Jon Eigill Johansen, et al., "Bacterial Carotenoids LI$^x$ c$_{50}$-Carotenoids 17$^{xx}$ Total Synthesis of Two Bacterioruberin Derivatives Absolute Configuration of Bacterioruberin," Tetrahedron Letters, No. 12, 1976, pp. 955-958.

International Search Report issued Jun. 10, 2014 in PCT/JP2014/055802 filed Mar. 6, 2014.

*Primary Examiner* — Sikarl Witherspoon
(74) *Attorney, Agent, or Firm* — Oblon, McClelland, Maier & Neustadt, L.L.P.

(57) ABSTRACT

Provided is a method of producing lavandulal at a high yield by controlling formation of its isomer of lavandulal as a by-product.

In a method of producing lavandulal by making an acetal compound represented by the following formula (I) react with 3-methyl-1-butene-3-ol in the presence of an acid catalyst, the method includes: adding, to a liquid mixture comprising an acid catalyst, an acetal compound represented by the following formula (I), and 3-methyl-1-butene-3-ol in at least a portion of an amount to be used (3-methyl-1-butene-3-ol (a)), 3-methyl-1-butene-3-ol in the other portion of the amount to be used (3-methyl-1-butene-3-ol (b)); and maintaining the liquid mixture at a temperature of 110° C. or higher:

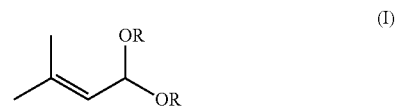

(I)

in which Each R in the formula (I) represents an alkyl group.

4 Claims, No Drawings

METHOD FOR PRODUCING LAVANDULAL

TECHNICAL FIELD

The present invention relates to a method for producing lavandulal. The lavandulal produced by the present method is useful as a raw material for medicines, agricultural chemicals, various kinds of chemical products and resins, and besides it is particularly suitable as a perfume material, notably a raw material of lavandulol having a fragrance like lavender.

BACKGROUND ART

Examples of a method for producing lavandulal include:
(1) a method of reducing lavandulic acid or its ester, synthesized by making a strong base act on acrylic ester of 3-methyl-1-butene-3-ol, through the use of an aluminum hydride compound (see Patent Document 1),
(2) a method of hydrolyzing lavandulal dimethylhydrazone synthesized by anionizing senecioaldehyde dimethylhydrazone with an organolithium compound and subjecting the obtained anion to coupling reaction with prenyl bromide (see Non-Patent Document 1),
(3) a method of carrying out hydrolysis after converting the dithioester corresponding to lavandulic acid into dithioacetal through the use of ethylmagnesium bromide (see Non-Patent Document 2),
(4) a method of hydrolyzing lavandulal acetal synthesized by coupling reaction between an iron complex and prenyl iodide (see Non-Patent Document 3),
(5) a method of oxidizing lavandulol with chromium oxide (see Non-Patent Document 4), and
(6) a method of making senecioaldehyde dialkyl acetal react with 3-methyl-1-butene-3-ol in the presence of an acid catalyst (see Patent Document 2).

RELATED ART DOCUMENTS

Patent Documents

Patent Document 1: JP-B-47-30690
Patent Document 2: JP-A-2002-308815

Non-Patent Documents

Non-Patent Document 1: *Journal of Organic Chemistry*, vol. 62, p. 734, 1997
Non-Patent Document 2: *Tetrahedron*, vol. 40, p. 1573, 1984
Non-Patent Document 3: *Tetrahedron*, vol. 41, p. 5741, 1985
Non-Patent Document 4: *Tetrahedron Letters*, No. 12, p. 955, 1976

SUMMARY OF THE INVENTION

Problems that the Invention is to Solve

However, there have been problems that each of the above methods (1) to (5) requires the use of an expensive metallic reactant, and besides each of the above methods (1) to (4) requires the synthesis of lanvadulal to undergo many steps, while the method (5) uses hard-to-get lavandulol as a raw material. Therefore it has been difficult to produce lavandulal at low cost on a commercial scale in accordance with any of the above methods (1) to (5).

The above method (6) has been suggested in order to solve the problems presented by the above methods (1) to (5), and in regard thereto it has been disclosed that lavandulal can be produced simply and easily from a readily available raw material at low cost as compared with the cases using the above methods (1) to (5). However, according to detailed analysis of the method (6) by the present inventor, and more specifically, detailed analysis on the basis of the disclosure of Example 1 in the Patent Document 2, it turned out that an isomer of lavandulal (hereafter referred to as isoLVAL) was produced as a by-product in an amount of the order of 10% (see Reference Example 1 mentioned later). Such isoLVAL has the following structural formula:

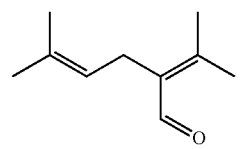

and the boiling point thereof is 235° C./101.3 KPa (760 mmHg) close to the boiling point of lavandulal (200° C./101.3 KPa (760 mmHg)). Thus, in the purification by reduced-pressure distillation, their closer boiling points made it difficult to achieve perfect separation of isoLVAL from lavandulal. In other words, it has turned out that the above method (6) still had room for improvement from the viewpoint of producing lavandulal with a high purity as required for a perfume purpose on an industrial scale, and that at a high yield.

An object of the invention is therefore to provide a method which allows producing of lavandulal, ideally lavandulal having such a high purity as required for a perfume purpose, with industrial advantage at a high yield and a low cost.

Means for Solving the Invention

In view of presumed formation mechanisms of isoLVAL in the above method (6), intensive studies have been made with respect to reaction methods capable of reducing the amount of isoLVAL formed as a by-product to the minimum. Surprisingly, these studies have produced a finding that, when a technique was adopted that, at the occasion of making an acetal of a specific structure (e.g. senecioaldehyde dialkylacetal) react with 3-methyl-1-butene-3-ol in the presence of an acid catalyst, the temperature of the reaction system (liquid mixture) was maintained no lower than the specified range, and besides 3-methyl-1-butene-3-ol, in a portion of the amount to be used, had been added in advance to the reaction system, and the remaining amount of 3-methyl-1-butene-3-ol was added to the resulting reaction system, it was possible not only to elevate the yield rate of lavandulal as the intended product to 70% or higher but also to reduce the formation rate of isoLVAL as a by-product to 5% or lower, thereby resulting in the completion of the invention.

That is, the invention can be achieved by the followings.
[1] A method of producing lavandulal by making an acetal compound represented by the following formula (I) react with 3-methyl-1-butene-3-ol in the presence of an acid catalyst, the method comprising:
adding, to a liquid mixture comprising an acid catalyst, an acetal compound represented by the following formula (I), and 3-methyl-1-butene-3-ol in at least a portion of an amount to be used (3-methyl-1-butene-3-ol (a)), 3-methyl-1-butene-3-ol in the other portion of the amount to be used (3-methyl-1-butene-3-ol (b)); and maintaining the liquid mixture at a temperature of 110° C. or higher:

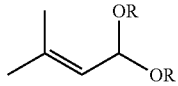

wherein each R in the formula (I) represents an alkyl group.

[2] The method of producing lavandulal according to [1], wherein an amount of the 3-methyl-1-butene-3-ol (a) used is in a range of 0.001 mole to 1.1 mole per mole of the acetal compound.

[3] The method of producing lavandulal according to [1] or [2], wherein a total amount of the 3-methyl-1-butene-3-ol (a) and the 3-methyl-1-butene-3-ol (b) is from 0.1 to 10 times by mole the amount of the acetal compound.

[4] The method of producing lavandulal according to any one of [1] to [3], wherein the acid catalyst has a concentration of 0.01 to 10 mass % with respect to the acetal compound.

Advantage of the Invention

According to the invention, lavandulal which is useful as a raw material for medicines, agriculture chemicals, various kinds of chemical products and resins, and besides which is particularly suitable as a perfume material, notably a raw material of lavandulol having a fragrance like lavender, can be produced with industrial advantage at a high purity as required for a perfume purpose, a high yield and a low cost.

Mode for Carrying Out the Invention

The acetal (I) for use in a producing method of the invention is a readily available compound, and can be produced with ease e.g. from senecioaldehyde.

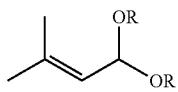

R in the formula (I) represents an alkyl group, preferably an alkyl group having a carbon number of 1 to 4, with examples including a methyl group, an ethyl group, a propyl group, an isopropyl group and a butyl group. Of these alkyl groups, a methyl group and an ethyl group, notably a methyl group, are preferred over the others.

The acid catalyst for use in the producing method of the invention has no particular restrictions so long as it is an acidic compound, and examples thereof include inorganic acids, such as hydrochloric acid, sulfuric acid and phosphoric acid; carboxylic acids, such as benzoic acid, terephthalic acid and trifluoroacetic acid; sulfonic acids, such as methanesulfonic acid, toluenesulfonic acid and trifluoromethanesulfonic acid; acidic salts such as pyridinium toluenesulfonate; and acid-type ion-exchange resins. Of these compounds, carboxylic acids, notably terephthalic acid, are preferred over the others from the viewpoints of availability and influence upon reaction apparatus.

In general it is appropriate that the amount of such an acid catalyst used be in a range of 0.01 mass % to 10 mass %, preferably 0.05 mass % to 1 mass %, with respect to the acetal (I). The liquid mixture may contain in advance the acid catalyst in the total amount to be used, or the liquid mixture may contain in advance the acid catalyst in a portion of the amount to be used, and thereto the remainder of the acid catalyst may be added later.

3-Methyl-1-butene-3-ol for use in the producing method of the invention is available with ease, and can be readily produced e.g. from 3-methyl-1-butyne-3-ol.

Although the total amount of 3-methyl-1-butene-3-ol to be used has no limits in the strict sense, the suitable range thereof is generally from 0.1 to 10 times by mole, preferably from 1 to 5 times by mole, that of the acetal (I).

In the producing method of the invention, it is required that to a liquid mixture containing an acid catalyst, an acetal compound of formula (I) and 3-methyl-1-butene-3-ol in at least a portion of the amount to be used (3-methyl-1-butene-3-ol (a)), 3-methyl-1-butene-3-ol in the other portion of the amount to be used (3-methyl-1-butene-3-ol (b)) is added, and besides the liquid mixture is maintained at a temperature of 110° C. or higher. In other words, it is important that 3-methyl-1-butene-3-ol in at least a portion of the amount to be used (3-methyl-1-butene-3-ol (a)), together with an acid catalyst and the acetal (I), is incorporated in advance into the reaction system, and then thereto be added 3-methyl-1-butene-3-ol in the other portion of the amount to be used (3-methyl-1-butene-3-ol (b)) so that the reaction liquid mixture can be maintained at a temperature of 110° C. or higher. The sum of the amounts of 3-methyl-1-butene-3-ol (a) and 3-methyl-1-butene-3-ol (b) is the total amount of 3-methyl-1-butene-3-ol to be used. The adoption of such a reaction scheme not only provides improvement in yield of the intended lavandulal but also allows for the first time a reduction to 5% or below in amount of isoLVAL formed as a by-product, which is a compound difficult to separate completely by purification through distillation and causing problems in perfume use in particular when it remains in a lavandulal product.

The suitable amount of 3-methyl-1-butene-3-ol (a) incorporated in advance, together with an acid catalyst and the acetal (I), into the reaction system is from 0.001 to 1.1 mole, preferably from 0.1 to 1.0 mole, per mole of the acetal (I).

In the producing method of the invention, important is the temperature at which the acetal (I) is made to react with 3-methyl-1-butene-3-ol in the presence of an acid catalyst, and it is required to control the reaction so that the temperature of the reaction mixture is maintained at 110° C. or higher, preferably in a range of 110° C. to 130° C. Examples of a specific method by which the reaction temperature of the reaction mixture is maintained at 110° C. or higher include a method of choosing the amount of 3-methyl-1-butene-3-ol (a) to be incorporated in advance, a method of controlling the speed at which 3-methyl-1-butene-3-ol (b), the other portion of 3-methyl-1-butene-3-ol to be used in the reaction, is added to the reaction liquid mixture, a method of controlling the temperature of 3-methyl-1-butene-3-ol (b), a method of controlling the temperature at which the reaction system is heated from the outside, and a method of controlling the pressure of the reaction system.

In the producing method of the invention, together with lavandulal, an alcohol (e.g. methanol in the case of using senecioaldehyde dimethylacetal as the acetal (I)) is produced secondarily in the reaction between the acetal (I) and 3-methyl-1-butene-3-ol. From the viewpoint of improving the reaction yield, it is appropriate to adopt a method of performing the reaction while removing the alcohol, together with lavandulal, into the outside of the reaction system by distillation. In the case of performing the reaction while removing the alcohol into the outside of the reaction system, it is preferred that the addition of 3-methyl-1-butene-3-ol (b) to the reaction system is controlled so that the alcohol concentration in the reaction liquid mixture can be reduced to 1.0 mass % or lower. On the other hand, there is no particular limitation on the reaction pressure, and the reaction may be carried out under any of reduced pressure, normal pressure and pressurized conditions. However, from the viewpoint of making it easy to maintain the temperature of reaction liquid mixture at 110° C. or higher, reduced pressure or normal pressure is preferred, and the pressure in a range of 13.3 kPa to 101.3 kPa is far preferred.

In the producing method of the invention, from the viewpoint of inhibiting the oxidation of lavandulal as a product, it is appropriate that the reaction is carried out in an atmosphere of inert gas such as nitrogen or argon.

In the producing method of the invention, the reaction may be performed in the presence or absence of a solvent. As to the solvent usable in the case of performing the reaction in the presence thereof, no particular limitation is placed so long as it does not participate in the reaction. Examples of the solvent usable therein include aliphatic hydrocarbons, such as pentane, hexane and heptane; aromatic hydrocarbons, such as benzene, toluene and xylene; halogenated hydrocarbons, such as methylene chloride, dichloroethane and chloroform; and ethers such as diethyl ether, diisopropyl ether and tetrahydrofuran. In the case of carrying out the reaction in the presence of a solvent, the suitable amount of solvent to be used is generally from 10 mass % to 99 mass %, preferably from 20 mass % to 80 mass %, far preferably from 30 mass % to 70 mass %, with respect to the total amount of the reaction liquid mixture. Depending on the kind of the solvent, there may be a case where the solvent and the alcohol produced together with lavandulal form an azeotrope. In such a case, the alcohol can also be removed into the outside of the reaction system by forming an azeotrope together with the solvent. By the way, from the viewpoint of the productivity of lavandulal and adjustment of the reaction liquid mixture during the reaction to a temperature of 110° C. or higher, it is preferred that the present producing method is carried out without using any solvent.

The producing method of the invention preferably includes: charging into a batch-type reaction vessel an acid catalyst, the acetal (I) and 3-methyl-1-butene-3-ol in at least a portion of the amount to be used (3-methyl-1-butene-3-ol (a)), and further a solvent if desired; heating this mixture up to a temperature of 110° C. or higher; and continuously or intermittently adding 3-methyl-1-butene-3-ol in the other portion of the amount to be used (3-methyl-1-butene-3-ol (b)). By the way, it is more advantageous to use a batch reaction vessel provided with a distillation unit and to perform the reaction while removing the produced alcohol into the outside of the reaction system.

The lavandulal produced at the conclusion of the reaction can be isolated by a method used generally for isolation and purification of organic compounds. For example, the intended lavandulal can be obtained by carrying out reduced-pressure distillation after neutralization of the reaction mixture. According to the producing method of the invention, isoLVAL is produced in a significantly small amount on the order of less than 5% as compared with the amount on the order of 10% attained by hitherto-known methods, and hence lavandulal of high purity required for perfume use in particular can be obtained in a high yield.

EXAMPLES

The invention will now be illustrated in more detail by reference to the following Reference Example, Examples and Comparative Example. However, the invention should not be construed as being limited to these Examples.

Reference Example 1

Into a reaction vessel provided with a stirrer, a distillation column and a thermometer were charged 39.5 g (0.30 mol) of senecioaldehyde dimethyl acetal, 46.1 g (0.53 mol) of 3-methyl-1-butene-3-ol and 0.1151 g (0.7 mmol) of terephthalic acid, and the temperature of the mixture inside the reaction vessel was raised to 105° C. by heating under stirring. Then, while removing by distillation the methanol produced via the head of the distillation column the mixture inside the reaction vessel was stirred for 11 hours in a temperature range of 105° C. to 109° C. Although the reaction was performed as the methanol produced was removed by distillation, the final temperature did not reach to 110° C. When the thus obtained reaction solution was cooled and then analyzed by gas chromatography, it was found that lavandulal was produced in an amount of 31.1 g (0.204 mol) at a 68% yield and isoLVAL was produced in an amount of 3.5 g (0.023 mol) at a 7.7% yield. By purification of the reaction solution by distillation, lavandulal was obtained in an amount of 24.9 g (0.163 mol) at a 54% cumulative yield with a 9.3% isoLVAL content.

Example 1

Into a reaction vessel provided with a stirrer, a distillation column and a thermometer were charged 39.8 g (0.30 mol) of senecioaldehyde dimethyl acetal, 12.97 g (0.15 mol) of 3-methyl-1-butene-3-ol and 0.1161 g (0.7 mmol) of terephthalic acid, and the temperature of the mixture inside the reaction vessel was raised to 118° C. by heating under stirring. Thereto, 33.03 g (0.38 mol) of 3-methyl-1-butene-3-ol was added dropwise over 4 hours. From the start of the dropwise addition of 3-methyl-1-butene-3-ol, the methanol produced via the head of the distillation column was removed by distillation, and the mixture inside the reaction vessel was stirred for 9 hours in a temperature range of 114° C. to 123° C. When the thus obtained reaction solution was cooled and then analyzed by gas chromatography, it was found that lavandulal was produced in an amount of 34.7 g (0.228 mol) at a 76% yield and isoLVAL was produced in an amount of 1.3 g (0.009 mol) at a 2.8% yield. By purification of the reaction solution by distillation, lavandulal was obtained in an amount of 31.1 g (0.204 mol) at a 68% cumulative yield with a 0.5% isoLVAL content.

Example 2

Into a reaction vessel provided with a stirrer, a distillation column and a thermometer were charged 40.4 g (0.31 mol) of senecioaldehyde dimethyl acetal, 25.84 g (0.30 mol) of 3-methyl-1-butene-3-ol and 0.1168 g (0.7 mmol) of terephthalic acid, and the temperature of the mixture inside the reaction vessel was raised to 110° C. by heating under stirring. Thereto, 20.98 g (0.24 mol) of 3-methyl-1-butene-3-ol was added dropwise over 2.5 hours. From the start of the dropwise addition of 3-methyl-1-butene-3-ol, the methanol produced via the head of the distillation column was removed by distillation, and the mixture inside the reaction vessel was stirred for 9 hours in a temperature range of 110° C. to 122° C. When the thus obtained reaction solution was cooled and then analyzed by gas chromatography, it was found that lavandulal was produced in an amount of 34.15 g (0.224 mol) at a 73% yield and isoLVAL was produced in an amount of 1.4 g (0.009 mol) at a 3.0% yield. By purification of the reaction solution by distillation, lavandulal was obtained in an amount of 30.74 g (0.202 mol) at a 65% cumulative yield with a 0.6% isoLVAL content.

Comparative Example 1

Into a reaction vessel provided with a stirrer, a distillation column and a thermometer were charged 46.30 g (0.53 mol) of 3-methyl-1-butene-3-ol and 0.1133 g (0.7 mmol) of terephthalic acid, and the temperature of the mixture inside the reaction vessel was raised to 97° C. by heating under stirring. Thereto, 40.1 g (0.30 mol) of senecioaldehyde dimethyl acetal was added dropwise over 5 hours. From the start of the dropwise addition of senecioaldehyde dimethyl acetal, the methanol produced via the head of the distillation column was removed by distillation, and the mixture inside the reaction vessel was stirred for 15 hours in a temperature range of 97° C. to 122° C. When the thus obtained reaction solution was cooled and then analyzed by gas chromatography, it was found that lavandulal was produced in an amount of 28.3 g (0.186 mol) in a 62% yield and isoLVAL was produced in an amount of 3.0 g (0.020 mol) in a 6.7% yield. By purification of the reaction solution by distillation, lavandulal was obtained in an amount of 22.5 g (0.148 mol) at a 49% cumulative yield with a 8.1% isoLVAL content <Sensory Testing>

The lavandulal products obtained in Reference Example 1, Examples 1 and 2 and Comparative Example 1, respectively, were subjected to a reduction operation using an excess of sodium borohydride, and thereby their individual lavandulol products were obtained. Five professional panelists carried out sensory testing for each of the lavandulol products. The lavender fragrance of each lavandulol product was rated on a scale of 1 to 5 with reference to the lavender fragrance of lavandulol with 99.95% purity. Where the following evaluation criteria on a 1-to-5 scale were concerned, cases where products were rated as A or B by at least 3 panelists were regarded as passing, and the other cases were regarded as failing. Results obtained are shown in Table 1.

Evaluation Criteria
A: No nasty smell is noticed at all
B: A nasty smell is barely noticed
C: A nasty smell noticed is faint, but the kind thereof is perceptible
D: The kind of a nasty smell noticed is easily perceptible
E: A strong nasty smell is noticed

TABLE 1

|  | Reference Example 1 | Example 1 | Example 2 | Comparative Example 1 |
|---|---|---|---|---|
| lavender fragrance | failing | passing | passing | failing |

INDUSTRIAL APPLICABILITY

According to the invention, lavandulal not only useful as a raw material for medicines, agricultural chemicals, various kinds of chemical products and resins but also particularly suitable as a perfume material, notably a raw material of lavandulol having a fragrance like lavender, can be produced to industrial advantage at such a high purity as required for a perfume purpose, a high yield and a low cost.

While the invention has been described above in detail and by reference to specific embodiments thereof, it will be apparent to one skilled in the art that various changes and modifications can be made therein without departing from the spirit and scope thereof.

The present application is based on Japanese Patent Application No. 2013-56647 filed on Mar. 19, 2013, the entire contents of which are incorporated herein by reference.

The invention claimed is:

1. A method of producing lavandulal by reacting an acetal compound of formula (I) with 3-methyl-1-butene-3-ol in the presence of an acid catalyst, the method comprising:
    adding, to a liquid mixture comprising an acid catalyst, an acetal compound of formula (I), and 3-methyl-1-butene-3-ol in at least a portion of an amount to be used (3-methyl-1-butene-3-ol (a)), 3-methyl-1-butene-3-ol in the other portion of the amount to be used (3-methyl-1-butene-3-ol (b)); and
    maintaining the liquid mixture at a temperature of 110° C. or higher:

(I)

wherein each R in the formula (I) is an alkyl group.

2. The method of claim 1, wherein an amount of the 3-methyl-1-butene-3-ol (a) used is in a range of 0.001 mole to 1.1 mole per mole of the acetal compound.

3. The method of claim 1, wherein a total amount of the 3-methyl-1-butene-3-ol (a) and the 3-methyl-1-butene-3-ol (b) is from 0.1 to 10 times by mole the amount of the acetal compound.

4. The method of claim 1, wherein the acid catalyst has a concentration of 0.01 to 10 mass % with respect to the acetal compound.

* * * * *